United States Patent [19]

Lang et al.

[11] Patent Number: 5,294,608
[45] Date of Patent: Mar. 15, 1994

[54] GUANIDINOALKYL-1,1-BISPHOSPHONIC ACID DERIVATIVES, PROCESS FOR THEIR PREPARATION AND THEIR USE

[75] Inventors: Hans-Jochen Lang, Hofheim am Taunus; Christoph Naumann, Niedernhausen, both of Fed. Rep. of Germany; Denis Carniato, Clamart; Anne-Marie Moura, Moura, both of France; Ryoichi Satoh; Masakazu Katoh, both of Saitama, Japan

[73] Assignee: Hoechst Aktiengesellschaft, Frankfurt am Main, Fed. Rep. of Germany

[21] Appl. No.: 988,890

[22] Filed: Dec. 10, 1992

[30] Foreign Application Priority Data

Dec. 12, 1991 [DE] Fed. Rep. of Germany ....... 4140908
Apr. 9, 1992 [DE] Fed. Rep. of Germany ....... 4211976

[51] Int. Cl.⁵ ............... A61K 31/66; A61K 31/675; C07F 9/40; C07F 9/38; C07F 9/6506
[52] U.S. Cl. .................... 514/108; 514/80; 548/113; 558/157; 558/158; 558/159; 562/13
[58] Field of Search .............. 562/13; 558/157, 158, 558/159; 548/113; 514/80, 108

[56] References Cited

U.S. PATENT DOCUMENTS

| | | | |
|---|---|---|---|
| 4,645,762 | 2/1987 | Biere et al. | 514/108 |
| 4,857,513 | 8/1989 | Oku et al. | 514/76 |
| 4,963,536 | 10/1990 | Oku et al. | 514/76 |
| 4,990,503 | 2/1991 | Isomura et al. | 514/80 |
| 5,039,669 | 8/1991 | Isomura et al. | 514/80 |

FOREIGN PATENT DOCUMENTS

| | | |
|---|---|---|
| 243173A2 | 10/1987 | European Pat. Off. |
| 282309A3 | 9/1988 | European Pat. Off. |
| 0298553A1 | 1/1989 | European Pat. Off. |
| 354806A3 | 2/1990 | European Pat. Off. |

OTHER PUBLICATIONS

Organische Phosphorverbindungen 75, Herstellung und Eigenschaften von Aminomethylendiphosphinaten und –diphosphonaten, RR¹NCH [P(O)R²(OR³)]₂ und Derivaten: Ludwig Maier; Phosphorus and Sulfur 11:311–322 (1981).

The Synthesis of Stereochemically Pure Peptide Derivatives by the Phythaloyl Method, John C. Sheehan et al.; Am. Soc.; 74:3822–3825 (1951).

Amino Acids, V. Phthalyl Derivatives; John H. Billman et al.; Am. Soc.; 70:1473–1474 (1948).

Recherches dans la série des diurétiques sulfamidés; A. Lespagnol et al.; Bull. Soc. Fra.; pp. 800–804; (1965).

*Primary Examiner*—Mary C. Lee
*Assistant Examiner*—Michael G. Ambrose
*Attorney, Agent, or Firm*—Finnegan, Henderson, Farabow, Garrett & Dunner

[57] ABSTRACT

The invention describes tautomeric compounds of the formula Ia, Ib or Ic

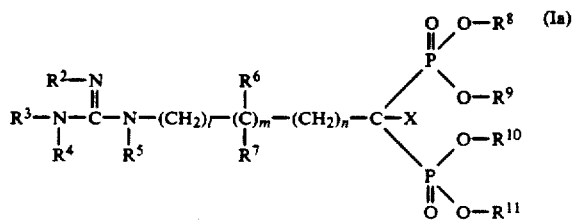

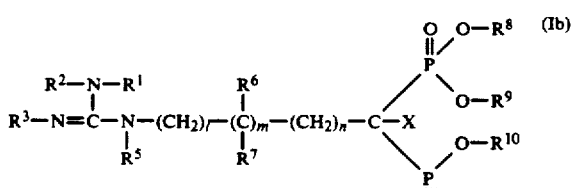

(Abstract continued on next page.)

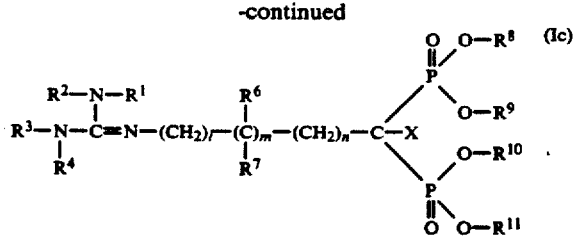

and/or their physiologically tolerable salts, in which $R^1$, $R^2$, $R^3$, $R^4$, $R^5$, $R^6$ and $R^7$ are a hydrogen atom, substituted $(C_1-C_7)$-alkyl, $(C_3-C_{10})$-cycloalkyl, substituted phenyl or $(C_1-C_4)$-alkylphenyl, $R^2$ is substituted phosphoric acid, $R^2$ and $R^3$, $R^2$ and $R^5$ or $R^4$ and $R^5$ form a monocyclic 5- to 7-membered saturated or unsaturated heterocyclic ring which is mono- or polysubstituted, $R^8$, $R^9$, $R^{10}$ and $R^{11}$ are a hydrogen atom or $(C_1-C_5)$-alkyl, X is a hydrogen atom, hydroxyl or halogen, l and n are an integer from 0 to 7, m is an integer from 0 to 2, and the sum of the numbers l, m and n is less than or equal to 10, a process for the preparation of the compounds of the formula Ia, Ib or Ic, pharmaceuticals and their use for the prophylaxis or treatment of osteoporosis.

9 Claims, No Drawings

GUANIDINOALKYL-1,1-BISPHOSPHONIC ACID DERIVATIVES, PROCESS FOR THEIR PREPARATION AND THEIR USE

DESCRIPTION

Osteoporosis is a commonly occurring bone disease. In the various forms of osteoporosis, a heavy loss of bony tissue occurs, so that finally the mechanical stability of the bone is lost. In healthy humans, the rate at which osteoclasts and osteoplasts are formed is such that bone formation and bone resorption are in equilibrium. In osteoporosis, the equilibrium is disturbed, so bone destruction occurs.

In the preparation of aminomethylenediphosphinates, L. Maier (Phosphorus and Sulfur, 1981, 11, pages 311-322) describes tetraethyl 1-((aminoiminomethyl)amino)methane-1,1-bisphosphonate as an intermediate compound. No use for this intermediate is given.

In the attempt to obtain active compounds with low side effects for the treatment and prophylaxis of osteoporosis, it has now surprisingly been found that the guanidinoalkyl-1,1-bisphosphonic acids according to the invention prevent bone resorption.

The invention therefore relates to the tautomeric compounds of the formulae Ia, Ib or Ic

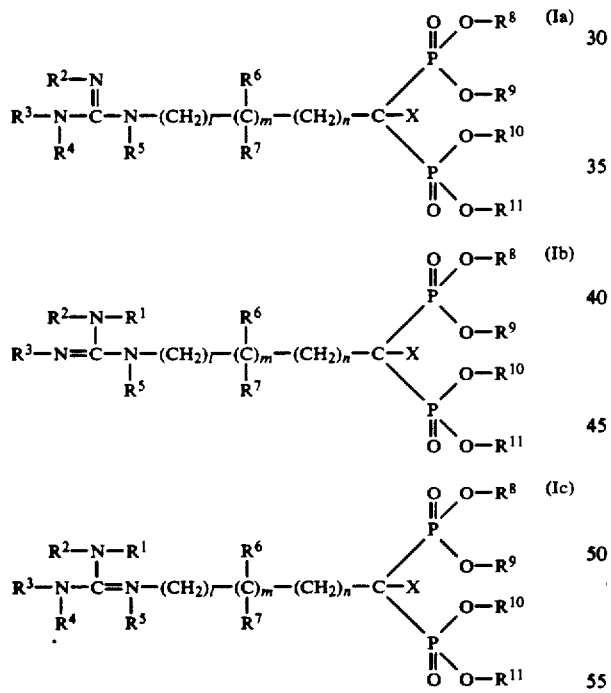

and/or a physiologically tolerable salt of the compound of the formulae Ia, Ib or Ic, in which $R^1$, $R^2$, $R^3$, $R^4$, $R^5$, $R^6$ and $R^7$ are identical or different and independently of one another have the meaning below a) a hydrogen atom,
b) $(C_1-C_7)$-alkyl, straight-chain or branched,
c) $(C_1-C_7)$-alkyl, straight-chain or branched, mono- or polysubstituted by
 1) a halogen atom such as a fluorine, chlorine or bromine atom,
d) $(C_3-C_{10})$-cycloalkyl,
e) $(C_3-C_{10})$-cycloalkyl, mono- or polysubstituted by
 1) $(C_1-C_4)$-alkyl, straight-chain or branched,
f) a radical of the formula II

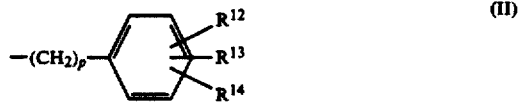

which $R^{12}$, $R^{13}$ and $R^{14}$ are identical or different and independently of one another have the meaning below 1) a hydrogen atom,
2) a halogen atom such as a fluorine, chlorine or bromine atom,
3) $(C_1-C_5)$-alkyl, straight-chain or branched,
4) $(C_1-C_5)$-alkyl, straight-chain or branched, mono- or polysubstituted by
 4.1 a halogen atom such as a fluorine, chlorine or bromine atom,
5) $-(SO_2)-CH_3$ or
6) $-O-CH_3$, and p is zero, 1, 2, 3 or 4 g) $R^2$ and $R^3$, $R^2$ and $R^5$ or $R^4$ and $R^5$, together with the two nitrogen atoms to which they are bonded, form 1) a monocyclic 5-, 6- or 7-membered heterocyclic ring, where the said ring is saturated or unsaturated and mono- or polysubstituted by
 1.1 a hydrogen atom,
 1.2 a halogen atom such as a fluorine, chlorine or bromine atom,
 1.3 $-O-(C_1-C_5)$-alkyl,
 1.4 oxo or
 1.5

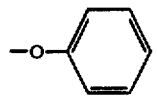

2) a bicyclic 9- or 10-membered heterocyclic ring system, where this ring system is unsaturated and mono- or polysubstituted as defined in g) 1.1 to g) 1.5 and/or 2 carbon atoms in this ring system are replaced by nitrogen atoms, or h) $R^1$ and $R^2$ or $R^3$ and $R^4$, together with the nitrogen atoms to which they are bonded, form a mono- or bicyclic 3- to 10-membered ring, where the ring is saturated or unsaturated and mono- or polysubstituted as defined in g) 1.1 to g) 1.5, i) $R^1$, $R^2$, $R^3$ or $R^4$ is a mono- or bicyclic 3- to 10-membered ring, where the ring is saturated or unsaturated and mono- or polysubstituted as defined in g) 1.1 to g) 1.5, $R^2$ is

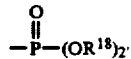

where $R^{18}$ is a) a hydrogen atom,
b) $(C_1-C_5)$-alkyl, straight-chain or branched, or
c) phenyl, l is an integer from 0 to 7,
m is zero, 1 or 2,
n is an integer from 0 to 7, the sum of the numbers l, m and n is equal to 10 or less than 10, $R^8$, $R^9$, $R^{10}$ and $R^{11}$ are identical or different and independently of one another have the meaning below
a) a hydrogen atom,
b) ($C_1$–$C_5$)-alkyl, straight-chain or branched, or
c) phenyl X is
a) a hydrogen atom,
b) hydroxyl,
c) a halogen atom such as a fluorine, chlorine or bromine atom, or
d) ($C_1$–$C_4$)-alkyl, in the case in which l, m and n are zero, excluding the compound tetraethyl 1-((aminoiminomethyl)amino)methane-1,1-bisphosphonate.

Preferred compounds of the formulae Ia, Ib or Ic and/or alkali metal, ammonium or triethylammonium salts of the compounds of the formulae Ia, Ib or Ic are those in which $R^1$, $R^2$, $R^3$, $R^4$, $R^5$, $R^6$ and $R^7$ are identical or different and independently of one another have the meaning below
a) a hydrogen atom,
($C_1$–$C_7$)-alkyl, straight-chain or branched,
($C_5$–$C_8$)-cycloalkyl,
d) a radical of the formula II,
  in which $R^{12}$, $R^{13}$ or $R^{14}$ are identical or different and independently of one another have the meaning below
1) a hydrogen atom,
2) a halogen atom such as a fluorine, chlorine or bromine atom,
3) ($C_1$–$C_5$)-alkyl, straight-chain or branched,
4) ($C_1$–$C_5$)-alkyl, straight-chain or branched, mono- or polysubstituted by
  4.1 a halogen atom such as a fluorine, chlorine or bromine atom,
5) —($SO_2$)—$CH_3$ or
6) —O—$CH_3$,
e) $R^2$ and $R^3$, $R^2$ and $R^5$ or $R^4$ and $R^5$, together with the two nitrogen atoms to which they are bonded, form
  1) a monocyclic 5-, 6- or 7-membered heterocyclic ring, where said ring is saturated or unsaturated and mono- or polysubstituted by
    1.1 a hydrogen atom,
    1.2 —O—($C_1$–$C_5$)-alkyl,
    1.3 oxo or
    1.4

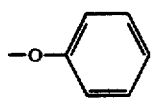

or
  2) a bicyclic 9- or 10-membered heterocyclic ring system, where this ring system is unsaturated and mono- or polysubstituted as defined in e) 1.1 to e) 1.4 and/or 2 carbon atoms in this range system are replaced by nitrogen atoms, or
f) $R^1$ and $R^2$ or $R^3$ and $R^4$, together with the nitrogen atoms to which they are bonded, form a mono- or bicyclic 3- to 10-membered ring, where the ring is saturated or unsaturated and mono- or polysubstituted as defined in e) 1.1 to e) 1.4, p is zero, 1, 2 or 3,
$R^2$ is

where $R^{18}$ is
a) a hydrogen atom or
b) ($C_1$–$C_4$)-alkyl, straight-chain or branched,
X is
a) a hydrogen atom or
b) hydroxyl,
l is an integer from 0 to 5,
m is zero or 1,
n is an integer from 0 to 5,
the sum of the numbers l, m and n is equal to 7 or less than 7,
$R^8$, $R^9$, $R^{10}$ and $R^{11}$ are identical or different and independently of one another have the following meaning
a) a hydrogen atom or
b) ($C_1$–$C_4$)-alkyl, straight-chain or branched.

Particularly preferred compounds of the formula Ia, Ib or Ic and/or sodium, potassium, ammonium or triethylammonium salts of the compounds of the formulae Ia, Ib or Ic are those
in which $R^1$ is
a) a hydrogen atom or
b) ($C_1$–$C_3$)-alkyl,
$R^2$ is
a) a hydrogen atom,
b) ($C_1$–$C_3$)-alkyl,
c) ($C_5$–$C_8$)-cycloalkyl or
d)

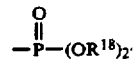

where $R^{18}$ is
1) a hydrogen atom or
2) ($C_1$–$C_4$)-alkyl,
$R^3$, $R^4$, $R^5$ or $R^7$ are a hydrogen atom, or
$R^2$ and $R^3$, $R^2$ and $R^5$ or $R^4$ and $R^5$, together with the two nitrogen atoms to which they are bonded, form a monocyclic 5-, 6- or 7-membered ring, where the ring is saturated or unsaturated, or
$R^1$ and $R^2$ or $R^3$ and $R^4$, together with the nitrogen atom to which they are bonded, form a mono- or bicyclic 3- to 10-membered ring, where the ring is saturated or unsaturated,
$R^6$ is
a) a hydrogen atom or
b) ($C_5$–$C_8$)-cycloalkyl, or
$R^8$, $R^9$, $R^{10}$ or $R^{11}$ are identical or different and independently of one another have the meaning below
a) a hydrogen atom,
b) ($C_1$–$C_4$)-alkyl,
X is a hydrogen atom or hydroxyl,
l is zero, 1, 2 or 3,
m is zero or 1,
n is zero, 1, 2 or 3
the sum of the numbers l, m or n is equal to 5 or less than 5.

Particularly preferred compounds are tetraethyl 2-((O,O-diisobutylphosphoryl)-(aminoiminomethyl)amino)ethane-1,1-bisphosphonate, 2-((aminoiminomethyl)amino)ethane-1,1-bisphosphonic acid, tetraethyl 4-((bis(1,1-dimethylethoxycarbonyl)aminoiminomethyl)amino)butane-1,1-bisphosphonate, tetraethyl 2-((benzimidazolaminoiminomethyl)amino)ethane-1,1-bisphosphonate, 2-((benzimidazolaminoiminomethyl)amino)ethane-1,1-bisphosphonic acid and 4-((aminoiminomethyl)amino)butane-1,1-bisphosphonic acid.

The monocyclic 5- to 7-membered heterocyclic ring which is saturated or unsaturated and contains 2 nitrogen atoms includes, for example, radicals which are derived from imidazole, pyrazoline, imidazoline, imidazolidine, pyrimidine or 1,3-diazepine.

The bicyclic 9- or 10-membered heterocyclic ring system which is unsaturated and in which 2 carbon atoms can be replaced by nitrogen atoms includes, for example, radicals which are derived from benzimidazole, quinazoline, pteridine or purine.

The mono- or bicyclic 3- to 10-membered ring which is saturated or unsaturated and contains 1 nitrogen atom includes, for example, radicals which are derived from aziridine, azirine, azetidine, azetine, pyrrole, pyrroline, pyrrolidine, pyridine, tetrahydropyridine, piperidine, azepine, indole, quinoline or isoquinoline.

The invention also relates to a process for the preparation of the compounds of the formulae Ia, Ib or Ic according to the invention.

The compounds according to the invention can be prepared as follows:

A) A compound of the formula IIIa

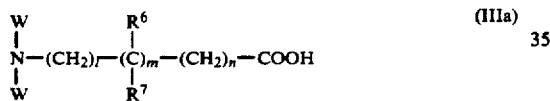

and/or the corresponding anhydride or acid chloride of the compound of the formula IIIa
where W is an amino-protective group and/or W has the abovementioned meaning of $R^6$, with the exception of a hydrogen atom, and $R^6$, $R^7$, l, m and n have the meaning mentioned in the formulae Ia, Ib or Ic, is reacted A1) with a compound of the formula IVa and/or IVb $P(OR^8)_3$ (IVa)

$P(OR^9)_3$ (IVb)

where $R^8$ and $R^9$ independently of one another are (C$_1$–C$_5$)-alkyl, straight-chain or branched, to give a compound of the formula IIIb

then the compound of the formula IIIb is reacted
A2) with a compound of the formula IVc and/or IVd $HP(O)(OR^{10})_2$ (IVc)

$P(OH)(OR^{11})_2$ (IVd)

to give a compound of the formula IIIc

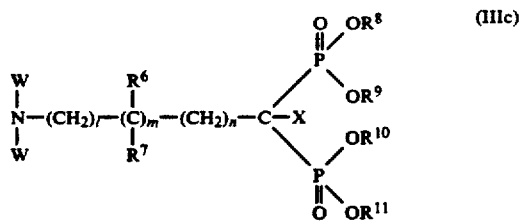

where $R^{10}$ and $R^{11}$ have the meaning mentioned in the formulae Ia, Ib or Ic and X is a hydrogen atom or hydroxyl, then, from the compound of the formula IIIc A3) the amino-protective group is removed, and the compound of the formulae IIId is obtained

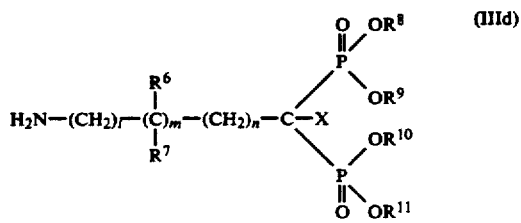

A4) then the compound of the formula IIId is reacted with a tautomeric compound of the formula Va or Vb

where Z is a radical of the group below
1) methylmercaptan,
2) ethylmercaptan or
3) 3,5-dimethylpyrazole-1-carboxyamidine nitrate and $R^1$, $R^2$, $R^3$ and $R^4$ have the meaning mentioned in formula Ia, Ib or Ic,
in the presence of an inert solvent to give the tautomeric compounds of the formula Ia, Ib or Ic, or B) a compound of the formula IIIa is reacted together with a compound of the formulae IVa, IVb, IVc or IVd in the presence of a dialkylamine to give the compound of the formula IIIc and, as described in A3) and A4), converted to a compound of the formulae Ia, Ib or Ic, or C) a compound of the formula IIIa is reacted with a phosphorylating agent to give a compound of the formula IIIc, where $R^8$, $R^9$, $R^{10}$ and $R^{11}$ are a hydrogen atom,
and then the compound of the formula IIIc is converted as described in A3) and A4) to give a compound of the formulae Ia, Ib or Ic, or D) a salt of the tautomeric compound of the formula VIa, VIb or VIc

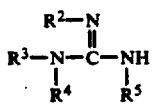
(VIa)

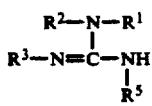
(VIb)

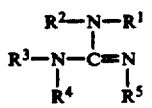
(VIc)

where $R^1$, $R^2$, $R^3$, $R^4$ and $R^5$ have the meaning mentioned in A1) to A4), is reacted in the presence of a compound of the formula VII

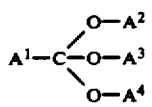
(VII)

where $A^1$ is
1) a hydrogen atom or
2) $(C_1-C_4)$-alkyl and
$A^2$, $A^3$ or $A^4$ is $(C_1-C_4)$-alkyl D1) with a compound of the formula IVc to give a compound of the formulae Ia, Ib or Ic, where $R^8$, $R^9$, $R^{10}$ and $R^{11}$ are $(C_1-C_5)$-alkyl, straight-chain or branched, and m, l and n are zero, and if appropriate D2) the bisphosphonic acid ester of the formulae Ia, Ib or Ic is converted into the corresponding bisphosphoric acid, or E) a compound of the formula VIII

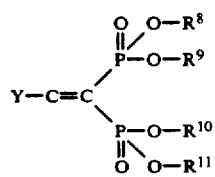
(VIII)

where $R^8$, $R^9$, $R^{10}$, $R^{11}$ have the meaning mentioned in A1) to A4) and Y has the meaning of $R^6$ and/or $R^7$, is reacted E1) with a compound of the formula IX, where Z is amino, in the presence of an inert solvent to give a compound of the formulae Ia, Ib or Ic, and if appropriate E2) the compound of the formulae Ia, Ib or Ic is reacted as described in D2), or F) a compound of the formula IX

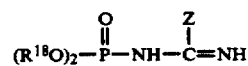
(IX)

where Z and $R^{18}$ have the meaning mentioned in A4), is reacted

F1) with a compound of the formula IIId to give a compound of the formulae Ia, Ib or Ic and then, if appropriate F2) reacted as described in D2), or G) a compound of the formula IIId is reacted with a compound of the formula X

(X)

where $R^1$ and $R^2$ independently of one another have the meaning of $R^6$, to give a compound of the formulae Ia, Ib or Ic, or H) a compound of the formula IIIc obtained according to process variant A2), where X is hydroxyl, is reacted with a thionyl halide to give a compound of the formula IIIc, where X is halogen, then this is further reacted as described in A3) and A4), or I) a compound of the formula VIII is reacted with a compound of the formula Va or Vb, where Z is amino, and $R^1$, $R^2$, $R^3$ and $R^4$ have the meaning mentioned in A4), to give a compound of the formulae Ia, Ib or Ic, or K) a compound of the formula IIId is reacted
K1) with a compound of the formula XI

(XI)

where V is an amino-protective group and/or V has the meaning of $R^1$, $R^2$, $R^3$, $R^4$ or $R^6$ as defined in A4), with the exception of a hydrogen atom, and the compound of the formula IIIe is obtained

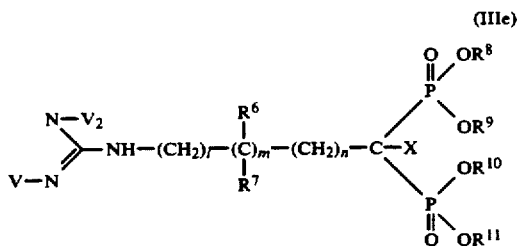
(IIIe)

K2) then the amino-protective group which may be present is removed, and a tautomeric compound of the formulae Ia, Ib or Ic is obtained, or L) the bisphosphonic acids of the formulae Ia, Ib or Ic obtained in D2), E2), F2) or K2) are converted into the corresponding salts by reaction with a physiologically tolerable base.

In process step A1), a procedure is best used in which the compound IIIa or the corresponding anhydride or acid chloride is reacted with a phosphonic acid triester of the formula IVa or IVb, if appropriate in the presence of a base, to give a compound of the formula IIIb.

The reaction temperatures are from 0° C. to 120° C., preferably from 0° C. to 80° C. The reaction times are about 1 to 6 hours, preferably 1 to 3 hours. The completion of the reaction can be determined, for example, by means of thin layer chromatography (TLC).

The starting substances of the formula IIIa necessary for this process step can be prepared, if they are not commercially available, in a simple manner by processes known from the literature (J. H. Billman, W. F. Harting, Am. Soc. 70, p. 1473 (1948)). Suitable amino-protective groups are, for example, phthaloyl or benzyloxycarbonyl radicals (T. W. Greene, Protective Groups in Organic Synthesis).

In process variant A2), a procedure is best used in which the compound of the formula IIIb) is reacted with a phosphorous acid diester of the formula IVc or IVd in the presence of a dialkylamine, for example diethylamine, or of an alkali metal alkoxide, for example sodium methoxide, to give the compound of the formula IIIc.

The reaction temperatures are from 0° C. to 120° C., preferably from 0° C. to 90° C. The reaction times are about 1 to 8 hours, preferably 1 to 4 hours. The completion of the reaction can be determined, for example, by means of TLC.

In process variant A3), the amino-protective group is best removed as follows, by heating the alcoholic solution to boiling point for 1 to 2 hours or incubating at room temperature for 1 to 2 days (J. C. Sheehan, Am. Soc. 74, p. 3822 (1952)).

In process variant A4), a procedure is best used in which the compound of the formula IIId is dissolved with a compound of the formula Va or Vb in a stoichiometric ratio in an inert solvent, for example toluene, dimethylformamide (DMF), dimethyl sulfoxide (DMSO), pyridine, tetrahydrofuran or dioxane, and reacted with heating.

The reaction temperatures are from 60° C. to 180° C., preferably from 80° C. to 120° C. The reaction times are about 1 to 22 hours, preferably 1 to 6 hours.

The completion of the reaction can be determined by TLC. The products of the reaction can be purified by column chromatography, for example on silica gel using a mixture of ethyl acetate and alcohol in a volume ratio of 5:1, or solely with alcohol as the eluent.

In process variant B), a procedure is best used in which the compound IIIa or the corresponding anhydride or acid chloride is reacted with a phosphorous acid ester of the formula IVa or IVb and a phosphorous acid diester of the formula IVc or IVd in the presence of a dialkylamine, for example diethylamine, or an alkali metal alkoxide, for example sodium methoxide, to give the compound IIIc.

The reaction temperatures are about 60° C. to 180° C., preferably 80° C. to 120° C. The reaction times are about 1 to 6 hours, preferably 1 to 3 hours.

The completion of the reaction can be determined by TLC. The products of the reaction can be purified by column chromatography on a silica gel column, for example using an eluent composed of ethyl acetate/ethanol in a volume ratio of 5:1 or with ethanol on its own.

Further reaction is carried out as described in process steps A3) and A4).

In process variant C), a procedure is best used in which a compound of the formula IIIa is reacted with a phosphorylating agent such as, for example, phosphorus trioxide or phosphorus trihalide as a mixture with phosphorous acid or phosphoric acid, phosphorus oxychloride or phosphorus pentachloride as well as phosphorus trichloride and chlorine, to give a compound of the formula IIIc. Phosphorus trioxide is preferred, and is preferably formed in situ by reaction of phosphorus trichloride with phosphorous acid or by reaction of excess phosphorus trichloride with aqueous phosphoric acid, for example with commercially available about 75% strength to about 95% strength, preferably about 85% strength phosphoric acid. The reaction is advantageously carried out with heating, for example to about 70° C. to about 120° C., in a suitable solvent such as tetrachloroethane, trichloroethane, chlorobenzene, chlorotoluene or liquid paraffin or without solvent and subsequently with hydrolytic working-up. Further reaction is carried out as described in A3) and A4).

In process variant D1), a procedure is best used in which the compounds of the formulae VIa, VIb or VIc or their salts are reacted with a compound of the formula IVc in the presence of a compound of the formula VII. The reaction is carried out in a stoichiometric ratio.

A solvent is not absolutely necessary. The reaction can be carried out at about 100° to 200° C., preferably at 130° C. to 170° C., for 1 to 6, preferably 1 to 4, hours. It takes place with removal of the resulting alcohol by distillation. To isolate and to purify the reaction products of the formulae Ia, Ib or Ic, the reaction mixture can be purified on a silica gel column using an eluent mixture composed of ethyl acetate and alcohol, volume ratio for example 6:1. The compound of the formulae Ia, Ib or Ic obtained can be converted into the corresponding bisphosphonic acids by hydrolysis (process variant D2), for example by heating under reflux in concentrated hydrochloric acid, or by treatment with strong acids or trimethylsilyl halide in anhydrous solvents. Anhydrous hydrobromic acid in acetic acid can be used directly or after appropriate dilution, or trimethylsilyl iodide dissolved in a solvent such as carbon tetrachloride, dimethylformamide, chloroform or toluene is used. The hydrolysis can be carried out with cooling or heating, for example the ester can be reacted with a trimethylsilyl halide with cooling at −10° C. or below, and a partially hydrolysed product is obtained.

The guanidine precursors are prepared by methods known from the literature (A. Lespagenol, D. Bar, C. Lespasenol, A. Anovith; Bull. Soc. Fra. 1965, page 800 et seq.).

In process variant E), a procedure is best used in which the compound of the formula IX, where Z is amino, is reacted in an equimolar amount or in an excess of up to 3-fold, if appropriate in an inert solvent such as dimethyl sulfoxide (DMSO), dimethyl formamide (DMF), toluene, $(C_1-C_4)$-alkanol, tetrahydrofuran (THF) dioxane or diethyl ether, with a compound of the formula VIII with the addition of a base such as potassium carbonate, sodium carbonate, potassium hydroxide, triethylamine, diethylamine or alternatively also without the addition of a base to give a compound of the formulae Ia, Ib or Ic. The reaction temperatures are about 25° C. to 100° C., preferably when using a solvent 25° C. to the boiling point of the solvent, in particular 70° C. The reaction times are 6 to 48 hours, preferably 12 to 24 hours. The completion of the reaction can be determined, for example, by means of thin layer chromatography.

The purification of the reaction mixture can be carried out as described in process variant D1). Hydrolysis of the phosphoric acid ester of the compound of the formulae Ia, Ib or Ic is carried out as described in D2).

In the case of compound VIII, the starting compounds of process variant E) can be prepared in a simple manner by processes known from the literature (EP-A-0 298 553).

In process variant F), a procedure is used in which a compound of the formula (IX), where Z cannot be amino, is heated at about 60° to 180° C., preferably 80° to 120° C., with a compound of the formula (IIId) in an inert solvent such as, for example, toluene, dimethylformamide (DMF), dimethyl sulfoxide (DMSO), pyridine, tetrahydrofuran or dioxane. The compounds of the formulae Ia, Ib or Ic obtained in this manner can be purified by column chromatography as described in D) and converted into compounds of the formulae Ia, Ib and Ic by hydrolysis as described in process D2).

In process variant G) a procedure is best used in which a compound of the formula (IIId) is dissolved in 1N hydrochloric acid and the solution is evaporated. The residue is then taken up in an alcohol and treated with a compound of the formula X. The mixture is then heated to boiling and reacted to give a compound of the formulae Ia, Ib or Ic.

In process variant H), a procedure is best used in which the compound of the formula IIIc, where X is hydroxyl, is treated without solvent with thionyl chloride or an inert solvent such as dioxane, ether or toluene.

The reaction temperatures are 0° to 120° C., preferably 0° to 90° C. The reaction times are 1 to 8 hours, preferably 1 to 4 hours.

In process variant I), a procedure is used as described in variant E).

In process variant K1), a procedure is best used in which a compound of the formula IIId is reacted in equimolar amount or in an excess of up to 3-fold with a compound of the formula XI in an inert solvent such as DMSO, DMF, toluene, THF, dioxane or diethyl ether to give a compound of the formula IIIe.

The reaction temperatures are about 30° to 60° C., preferably 35° to 45° C. The reaction times are 1 to 4 days, preferably 30 to 70 hours, in particular 40 to 60 hours.

To isolate and purify the reaction products of the formula IIIe, the reaction mixture can be purified on a silica gel column using an eluent mixture composed of methylene chloride/methanol, volume ratio for example 98:2.

In process variant K2) the amino-protective group which may be present is best removed as follows, by heating an alcoholic solution of the compound of the formula IIIe at boiling point for 1 to 2 hours or heating to boiling with hydrochloric acid for about 12 hours.

In process variant L), a procedure is best used in which the compounds of the formulae Ia, Ib or Ic are neutralized at room temperature with the addition of a base, for example sodium hydroxide solution or potassium hydroxide solution, and the product is precipitated by addition of a solvent, for example ethanol or hexane.

The invention also relates to pharmaceuticals which contain at least one compound of the formulae Ia, Ib or Ic and/or at least one of the physiologically tolerable salts of the compound of the formulae Ia, Ib or Ic, tetraethyl 1-((aminoiminomethyl)amino)methane-1,1-bisphosphonate not being excepted, in addition to pharmaceutically suitable and physiologically tolerable auxiliaries and excipients, diluents and/or other active compounds.

The invention further relates to the use of compounds of the formulae Ia, Ib and/or Ic and/or their physiologically tolerable salts for the prophylaxis and treatment of osteoporosis.

The pharmaceuticals according to the invention can be administered topically, percutaneously, nasally, intravenously, inlramuscularly, intraperitoneally, subcutaneously, intraarticularly, periarticularly, rectally or orally.

The pharmaceuticals according to the invention for the prophylaxis and treatment of osteoporosis are prepared by bringing at least one compound of the formula Ia, Ib or Ic and/or one of its physiologically tolerable salts into a suitable administration form, if appropriate using auxiliaries and/or excipients. The auxiliaries and excipients are derived from the group comprising the vehicles, preservatives and other customary auxiliaries.

For example, for all administration forms auxiliaries such as starches, for example potato, corn or wheat starch, cellulose or its derivatives, in particular microcrystalline cellulose, silica, various sugars such as lactose, magnesium carbonate and/or calcium phosphates can be used. It is furthermore advantageous to add to the oral administration forms auxiliaries which improve the tolerability of the medicaments, such as, for example, mucilage-forming agents and resins. For better tolerability, the medicaments can also be administered in the form of capsules insoluble in gastric juice. Moreover, it may be advantageous to add to the administration form, or to a component of a combination preparation, a retarding agent, if appropriate in the form of permeable membranes, such as, for example, those based on a cellulose or polystyrene resin or ion exchangers.

The dosage of the pharmaceutical according to the invention to be used is dependent on various factors such as the administration form of the medicament and the condition, weight and severity of the disease of the patient. A daily dose of about 5,000 mg of the pharmaceuticals according to the invention should only be exceeded, however, for a short period. About 10 to 2,500 mg are preferred as a daily dose for a human of body weight 70 kg. The daily dose of the pharmaceuticals according to the invention can be carried out in the form of an individual administration or in several smaller doses. Administration in 3 to 8 doses per day is preferred.

The invention is illustrated in greater detail below by examples. The percentage data relate to percentages by volume, if not stated otherwise.

EXAMPLE 1

Preparation of diethyl guanidinophosphite 9.6 g (100 mmol) of guanidine hydrochloride are taken up in 8 g (200 mmol) of sodium hydroxide, which is dissolved in 50 ml of water, and 20 ml of ethanol and the mixture is cooled to 0° C. A solution of 13.8 g (100 mmol) of diethyl phosphite in 50 ml of carbon tetrachloride is added to this mixture and it is stirred at 25° C. for 24 hours. 30 ml of water are then added and the mixture is extracted with methylene chloride (3×30 ml). The organic phases are combined and dried ($K_2CO_3$). After concentrating on a rotary evaporator, an oil is obtained which partially crystallizes. The crude product is recrystallized from 100 ml of ethyl acetate. A colorless product is obtained after filtering with suction.

Yield: 5.7 g (24% of theory),

Melting point: 112°-113° C.,

Analysis: Calculated; C=30.6, H=7.2, N=21.4. Found: C=30.2, H=6.9, N=21.7.

$^{31}$P-NMR spectroscopy: ($D_2O$) $\delta P = 8.54$ ppm.

EXAMPLE 2

Preparation of diisobutyl guanidinophosphite 9.6 g (100 mmol) of guanidine hydrochloride are taken up in 8.0 g (200 mmol) of sodium hydroxide, which is dissolved in 50 ml of water, and 20 ml of ethanol and the mixture is cooled to 0° C. A solution of 16.2 g (834 mmol) of diisobutyl phosphite in 50 ml of carbon tetrachloride is added dropwise to this mixture in the course of 15 min. The cooling is then removed and the mixture is stirred at 25° C. for 4 hours. The organic phase is separated off and the aqueous phase obtained is extracted a further 2 times using 50 ml of chloroform each time. The combined extracts are dried with potassium carbonate.

After concentrating on a rotary evaporator and drying, 18.3 g of crude product are obtained, which is recrystallized from 180 ml of ethyl acetate.

Yield: 13.3 g (64.7% of theory).
Melting point: 152°-156° C.
Analysis: Calculated: C=43.0, H=8.83, N=16.7. Found: C=42.8, H=8.70, N=16.5.
$^1$H-NMR spectroscopy: (CDCl$_3$) 0.93 (d, 7.5 Hz, 12 H, aliphatic); 1.90 (mc, 2H, aliphatic); 3.65 (t, 7.5 Hz, 4 H, aliphatic).
$^{31}$P-NMR spectroscopy: (CDCl$_3$ $\delta$P=7.87 ppm.

EXAMPLE 3

Preparation of tetraethyl 2-((O,O-diisobutylphosphoryl)(aminoiminomethyl)amino)ethane-1,1-bisphosphonate 10 g (40 mmol) of diisobutyl guanidinophosphite and 12.4 g (41 mmol) of tetraethyl vinyldiphosphonate are dissolved in 150 ml of absolute tetrahydrofuran. 0.5 g of potassium carbonate is added to this mixture and it is heated to boiling for 8 hours. After filtering off solid material and concentrating on a rotary evaporator, 24 g of crude substance are obtained as an oil. The substance is chromatographed on a silica gel column. The eluent used is ethyl acetate containing 20% ethanol.

Yield: 11.4 g (51% of theory).
Analysis: Calculated: C=41.3, H=8.0, N=7.6. Found: C=41.1, H=8.0, N=7.4.
$^1$H-NMR spectroscopy: (CDCl$_3$) 0.95 (d, 7.5 Hz, 12H, aliphatic); 1.34 (mc, 12H, aliphatic); 1.92 (mc, 2H, aliphatic); 3.45 (mc, 1H); 3.82 (td, 2H); 3.74 (mc, 4H); 4, 10–4.28 (m, 8H, aliphatic).
$^{31}$P-NMR spectroscopy: (CDCl$_3$) $\delta$P$_1$=9.11, $\delta$P$_2$=21.94 ppm.

EXAMPLE 4

Preparation of 2-phthaloylethane-1-monoethylphosphonate-1-bisethylphosphonate 30 g (146 mmol) of phthaloylglycine, 26.8 g (225 mmol) of thionyl chloride and 1 ml of dimethylformamide are initially introduced and heated at 50°-55° C. for 4 hours with vigorous stirring After evolution of gas is complete, the excess thionyl chloride is removed under reduced pressure.

49.9 g (300 mmol) of triethyl phosphite, 41.4 g (296 mmol) of diethyl phosphite and 2 g of triethylamine are then slowly added dropwise to the acid chloride obtained. By addition of said components, a reaction temperature of 60°-70° C. is reached. After addition, the reaction temperature is slowly raised to 115° C. in such a manner that the evolution of gas does not stop. After reaching 115° C., this temperature is maintained for a further hour and the low-boiling components are then removed at 80° C. in a high vacuum (about 10$^{-3}$ mm Hg). The crude product is purified on a silica gel column using ethyl acetate as the eluent. In this way, the pure substance is obtained as a pale yellow oil.

Yield: 28.4 g (46.1% of theory).
Analysis: Calculated, C=45.8, H=5.5, N=3.3. Found: C=46.1, H=5.5, N=3.7.
$^{31}$P-NMR spectroscopy: (CDCl$_3$, $\delta$P$_1$=−0.58, $\delta$P$_2$=16.63 ppm.

EXAMPLE 5

Preparation of 2-aminoethane-1-monoethylphosphonate-1-bisethylphosphonate 8 g (19.1 mmol) of 2-phthalolylethane-1-monoethylphosphonate-1-bisethylphosphonate are dissolved in 50 ml of ethanol and the solution is treated with 1.34 g (21.4 mmol) of hydrazine hydrate and heated to boiling for 1 hour. After removing the solvent, a color less residue remains. This is titrated at 0° C. in 35 ml of 5N acetic acid and the resulting precipitate is separated off. The filtrate is adjusted to pH 7 at 0° C. using 2N sodium hydroxide solution and extracted 3 times with 60 ml of methylene chloride. The aqueous phase is adjusted to pH 9 and extracted again 2 times with 50 ml of methylene chloride. The extracts are combined and washed 3 times with 80 ml of a 10 percent sodium chloride solution. The organic phase is then dried over magnesium sulfate, filtered and concentrated on a rotary evaporator. The crude product is purified on a silica gel column using ethanol as the eluent. In this way, the product is obtained as a pale yellow oil.

Yield: 3.4 g (61.8% of theory).
Analysis: Calculated: C=33.3, H=7.3, N=4.8. Found: C=33.6, H=7.1, N=4.6.
$^{31}$P-NMR spectroscopy: (CDCl$_3$ $\delta$P$_1$=−0.39, $\delta$P$_2$=18.85 ppm.

EXAMPLE 6

Preparation of 2-((aminoiminomethyl)amino)ethane-1,1-bisphosphonic acid 1 g (1.8 mmol) of tetraethyl 2-((O,O-diisobutylphosphoryl)-(aminoiminomethyl)amino)-ethane-1,1-bisphosphonate is heated at boiling point for 5 hours in 20 ml of concentrated hydrochloric acid. At the same time, ethanol which is formed is distilled off. Excess hydrochloric acid is then removed. The residual oil is stirred with 10% methanol in 30 ml of acetone and decanted off. It is then boiled with 20 ml of methanol/10% water and allowed to stand for 24 hours for crystallization. The colorless crystals are filtered off with suction and dried.

Yield: 0.35 g (79.5% of theory).
Melting point: 230° C. (with dec.).
Analysis: Calculated: C=14.6, H=4.5, N=17.0. Found: C=14.3, H=4.8, N=17.4.
$^1$H-NMR spectroscopy: (D$_2$O): 1.92 (tt, 1H); 3.54 (td, 2H).
$^{31}$P-NMR spectroscopy: (NaOD) $\delta$P$_1$=18.88 ppm.

EXAMPLE 7

Preparation of 4-((aminoiminomethyl)amino)butane-1,1-bisphosphonic acid

A solution of 0.69 g (2 mmol) of tetraethyl 4-aminobutane-1,1-bisphosphonate (according to DE 3,225,469 A1, 01.05.1984) and 0.402 g (2 mmol) of 3,5-dimethylpyrazole-1-carboxamidine nitrate in 10 ml of DMF is heated at boiling point for 3 hours. The DMF is then distilled off in vacuo and the residue is dissolved in a little water. After extraction with diethyl ether and ethyl acetate (the organic extracts are discarded), the aqueous phase is distilled in vacuo. A dark oil (0.89 g) remains. This is heated at boiling point for 8 hours in 15 ml of concentrated hydrochloric acid. The excess hydrochloric acid is distilled off and the residue is treated with a little water, DMF and acetone. The precipitate is filtered off with suction and dried in vacuo.

Yield: 137 mg.
Melting point: 190°–195° C.
Mass spectroscopy:
m/e=M+H+ =274.

EXAMPLE 8

Preparation of tetraethyl 2-(4-trifluoromethyl)phenylethene-1,1-bisphosphonate 50 ml of absolute tetrahydrofuran are cooled to −10° C. and 7.42 g (39 mmol) of titanium tetrachloride are slowly added dropwise. 2.84 g (16.3 mmol) of p-trifluoromethylbenzaldehyde and 5.63 g (19.6 mmol) of tetraethyl methanediphosphonate are added to this mixture and the reaction temperature is allowed to rise to 0° C. 7.75 g (76.6 mmol) of triethylamine are then added dropwise to the reaction mixture, the temperature not rising above 5° C. The mixture is then stirred at room temperature for 3 hours and 100 ml of ice/water are then added. The mixture obtained is extracted with diethyl ether (3×200 ml). The combined ether extracts are washed with water until the extract is neutral. The ether phase is then washed with a saturated sodium chloride solution and dried over sodium sulfate. The crude product is purified on a silica gel column using acetone. A pale yellow oil is obtained.

Yield: 2.5 g (34.7% of theory).
Analysis: Calculated: C=45.9, H=5.6. Found: C=46.4, H=5.3.
$^1$H-NMR spectroscopy: (CDCl$_3$) 1.14–1.43 (m, 12H); 3.94–4.32 (m, 8H); 7.64–7.84 (m, 4H, aromatic); 8.18–8.45 (m, 1H, aliphatic).

EXAMPLE 9

Preparation of tetraethyl N,N-dibenzylaminomethane-1,1-bisphosphonate 97.3 g (1 mol) of dibenzylamine and 171.9 g (1.16 mol) of ethyl orthoformate and 290 g (2.1 mol) of diethyl phosphite are heated to 150° C. in the course of 3 hours with simultaneous removal of ethanol by distillation. The low-boiling components are then removed in a high vacuum (about 10$^{-3}$ mm Hg) and the crude product is purified on a silica gel column using ethyl acetate as the eluent. 197 g of crude product are obtained. 60 g are purified on a silica gel column using ethyl acetate as the eluent, the pure substance being obtained as a pale yellow oil.

Yield: 20.8 g (40.7% of theory).
Analysis: Calculated: C=57.1, H=7.3, N=2.9. Found: C=57.4, H=7.4, N=3.2.

EXAMPLE 10

Preparation of tetraethyl 1-aminomethane-1,1-bisphosphonate 17.1 g (35.4 mmol) of tetraethyl N,N-dibenzylaminomethane-1,1-bisphosphonate are dissolved in 170 ml of ethanol and 3.4 g of 5% strength Pd/C are added. Hydrogenation is carried out at normal pressure. After absorption of 100 ml of hydrogen, a further 3.4 g of 5% strength Pd/C are added and the hydrogenation is completed at normal pressure and room temperature (reaction time about 16 hours). The catalyst is then filtered off with suction. After removal of the solvent, 10.9 g of crude product are obtained. This is purified on a silica gel column using ethanol as the eluent.

Yield: 9.9 g (92.5% of theory).
Analysis: Calculated: C=35.7, H=7.7, N=4.6. Found: C=35.3, H=8.1, N=4.5.
$^{31}$P-NMR spectroscopy: (CDCl$_3$) δP=20.48 ppm.

EXAMPLE 11

Preparation of O,O-diisobutylphosphoryl S-ethyl isothiourea 18.5 g (0.1 mol) of S-ethylisothiourea hydrobromide are dissolved in 50 ml of water, 20 ml of ethanol and 8 g (0.2 mol) of sodium hydroxide and the solution is cooled to 0° C. A solution of 19.4 g (0.1 mol) of diisobutyl phosphite in 50 ml of carbon tetrachloride are added dropwise in the course of 10 min. After removal of the cooling, the reaction is allowed to come to room temperature and is stirred for a further 4 hours. After separating off the organic phase, the aqueous phase is extracted a further 2 times with 100 ml of chloroform and dried over potassium carbonate, filtered and concentrated on a rotary evaporator. O,O-diisobutylphosphoryl S-ethyl isothiourea is obtained as an orange-colored oil.

Yield: 24.9 g (84.1% of theory).
Analysis: Calculated: C=44.5, H=8.5, N=9.5. Found: C=44.8, H=8.1, N=9.3.
$^{31}$P-NMR spectroscopy: (CDCl$_3$) δP=4.29 ppm.

EXAMPLE 12

Preparation of 2-((Aminoiminomethyl)amino)ethane-1,1-bisphosphonic acid from 2-aminoethane-1-monoethylphosphonate-bisethylphosphonate 4 g (13.8 mmol) of 2-aminoethane-1-monoethylphosphonate-1-bisethylphosphonate and 4.15 g (14 mmol) of O,O-diisobutylphosphoryl S-ethyl isothiourea are dissolved in 40 ml of dimethylformamide (DMF) and the mixture is heated to boiling. After 6 hours, the DMF is removed and the crude mixture obtained is worked up and additionally processed as described in Example 3.

Yield: 1.8 g.
$^{31}$P-NMR spectroscopy: (NaOD) δP=18.9 ppm.

EXAMPLE 13

Synthesis of tetraethyl 4-((bis(1,1-dimethylethoxycarbonyl)aminoiminomethyl)amino)butane-1,1-bisphosphonate The precursor tetraethyl 4-aminobutane-1,1-bisphosphonate is prepared as described in DE 3,255,469 A1. N,N'-Bis(1,1-dimethylethoxycarbonyl)-S-methylisothiourea is prepared as described in the reference K. Niwak, Roczniki, Chem. Ber. 43 (1), 23, 1969.

A solution of 1.8 g (6.2 mmol) of N,N'-bis(1,1-dimethylethoxycarbonyl)-S-methylisothiourea and 4.4 g (12.7 mmol) of tetraethyl 4-aminobutane-1,1-bisphosphonate is heated at 40° C. for 2 days in 50 ml of tetrahydrofuran (THF). The organic phase is then washed with a saturated NaCl solution and dried over MgSO$_4$ and the THF is removed under reduced pressure. The crude product obtained is chromatographed on Florisil (60-100 mesh). The eluent consists of methylene chloride/methanol=98:2. In this way, 2.95 g (81%) of pure substance are obtained as a colorless oil.

IR spectroscopy: (CHCl$_3$) $\nu$=3300, 3285 (=C—NH); 1722, 1636 (C=O); 1617 (C=N) cm$^{-1}$.

$^1$H-NMR spectroscopy: (CDCl$_3$) 1.34 (t, 12H, OCH$_2$CH$_3$); 1.49 (s, 18H, CH$_3$); 1.8–2.1 (m, 4H, N—CH$_2$CH$_2$CH$_2$CH); 2.33 (tt, P—CH—P), 3.45 (m, 2H, N—CH$_2$); 4.19 (m, 8H, OCH$_2$CH$_3$).

EXAMPLE 14

Synthesis of 4-((aminoiminomethyl)amino)butane-1,1-bisphosphonic acid

A solution of 0.92 g (2.56 mmol) of tetraethyl 4-((bis(1,1-dimethylethoxycarbonyl)aminoiminomethyl)amino)butane-1,1-bisphosphonate in 15 ml of concentrated hydrochloric acid is heated at boiling point for 12 hours. After concentration, the residue is treated with ethanol. The precipitate is filtered off with suction under reduced pressure and dried under reduced pressure. It is recrystallized from ethanol/water.

Yield: 115 mg.
Melting point: 260° C.
Analysis: Calculated: C=21.8, H=5.5, N=15.3, P=22.4. Found: C=22.0, H=5.6, N=14.9, P=22.5.

$^1$H-NMR spectroscopy: (D$_2$O/NaOD) 1.60 (t, 1H, P—CH—P); 1.79 (m, 4H, CH$_2$CH$_2$); 3.11 (m, 2H, N—CH$_2$).

Mass spectroscopy: m/e=M+H$^+$=276.

EXAMPLE 15

Synthesis of tetraethyl 2-((benzimidazoylaminoiminomethyl)amino)ethane-1,1-bisphosphonate 2.0 g (11.4 mmol) of freshly recrystallized benzimidazoylguanidine are heated to boiling in 50 ml of ethanol for 30 minutes together with 3.4 g of tetraethyl ethylidine-1,1-bisphosphonate. The ethanol is then removed in vacuo. By addition of diethyl ether to the oil obtained, the desired product is obtained in the form of a colorless powder.

Yield: 4.9 g.
Melting point: 143° C.
Analysis: Calculated., C=45.47, H=6.57, N=3.10. Found: C=45.1, H=5.9, N=3.2.

$^1$H-NMR spectroscopy: (CDCl$_3$)/TMS) 1, 11–1.29 (m, 12H,OCH$_2$CH$_3$); 3.75–3.93 (tt, 1H, methine H); 3.96–4.11 (m, 8H, OCH$_2$CH$_3$); 4.50–4.61 (m, 2H, —CH$_2$—); 7.00–7.11 (2H, aromatic H); 7.18–7.29 (m, 1H, aromatic H); 7.36–7.43 (m, 1H, aromatic H).

$^{31}$P-NMR spectroscopy: (CDCl$_3$) 21.43 ppm.

EXAMPLE 16

Synthesis of 2-((benzimidazolylaminoiminomethyl)amino)ethane-1,1-bisphosphonic acid 1 g (2.1 mmol) of the substance from Example 15 is refluxed for 4.5 hours with 20 ml of concentrated hydrochloric acid. After removal of the excess hydrochloric acid in vacuo, the viscous oil obtained is crystallized from water. The target compound is obtained as a colorless powder.

Yield: 250 mg.
Melting point: >230° C.

Analysis: Calculated: C=33.07, H=4.16, N=19.28. Found: C=32.8, H=3.9, N=19.5.

$^1$H-NMR spectroscopy: (D$_2$O/NaOD): 2.63–2.83 (tt, 1H, methine H); 4.43–4.63 (m, 2H,—CH$_2$—); 7.00–7.09 (2H, aromatic H); 7.33–7.47 (1H, aromatic H); 7.57–7.70 (1H, aromatic H).

$^{31}$P-NMR spectroscopy:
(D$_2$O/NaOD) 18.55 ppm.

The activity of the compounds according to the invention is demonstrated in vitro in the following tests.

Bone resorption is determined by the analysis of $^{45}$Ca release from craniums of foetal rats which were 20 days old. The bones are labeled by injecting pregnant rats with 200 μCi/kg of $^{45}$CaCl$_2$ 2 days before the cranium of the foetuses is dissected.

1. Culturing of the bones

The cranium of the foetuses is divided into two halves. One half of the cranium is used as the control, the other half is incubated with the compounds according to the invention.

Each half of the cranium is cultured in a sterile plastic dish. The culture medium (BGJb Medium, Gibco) contains 10% foetal calf serum, penicillin-streptomycin (100,000 units/1, Gibco) and ascorbic acid (50 mg/1) per ml. The halves of the cranium are incubated at 37° C., in a gas atmosphere of 5% CO$_2$ and 95% O$_2$. After 24 hours, the culture medium is replaced by fresh medium, the compounds according to the invention and parathyroid hormone (10$^{-7}$M) are added and the mixture is incubated for 48 hours. Parathyroid hormone (10$^{-7}$M, Sigma) is added to the control.

At the end of the experiment, the activity of $^{45}$Ca in the culture medium and in the bone is determined.

The results in Table 1 show the inhibition of $^{45}$Ca release in the culture medium in percent. The results are the mean value of 3 to 5 experiments.

TABLE 1

| Preparation Example | Inhibition of $^{45}$Ca release | | |
| --- | --- | --- | --- |
| | Concentration of the preparations | | |
| | 10$^{-7}$ M | 10$^{-6}$ M | 10$^{-5}$ M |
| 6 | n.d. | 17.5% | 30.6% |
| 14 | 31% | 18% | n.e. | n.d. = not determined
n.e. = no effect

We claim:
1. A compound of the formula 1a, 1b or 1c

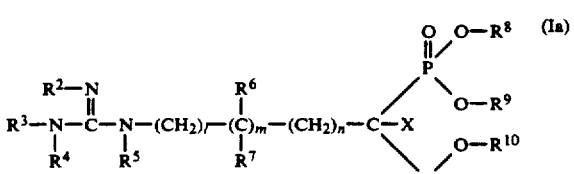

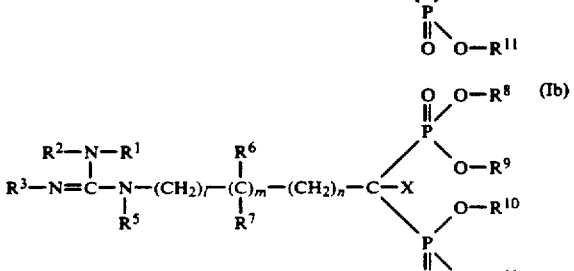

-continued

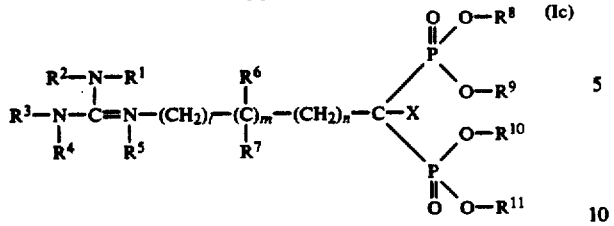

or a physiologically tolerable salt of the compound of the formula Ia, Ib or Ic, in which $R^1$, $R^2$, $R^3$, $R^4$, $R^5$, $R^6$ and $R^7$ are identical or different and independently of one another have the meaning below
a) a hydrogen atom,
b) $(C_1-C_7)$-alkyl, straight-chain or branched,
c) $(C_1-C_7)$-alkyl, straight-chain or branched, mono- or polysubstituted by
  1) a halogen atom,
d) $(C_3-C_{10})$-cycloalkyl,
e) $(C_3-C_{10})$-cycloalkyl, mono- or polysubstituted by
  1) $(C_1-C_4)$-alkyl, straight-chain or branched,
f) a radical of the formula II

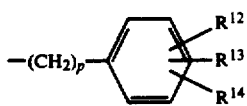

in which $R^{12}$, $R^{13}$ and $R^{14}$ are identical or different and independently of one another have the meaning below
1) a hydrogen atom,
2) a halogen atom,
3) $(C_1-C_5)$-alkyl, straight-chain or branched,
4) $(C_1-C_5)$-alkyl, straight-chain or branched, mono- or polysubstituted by
  4.1 a halogen atom,
5) $-(SO_2)-CH_3$ or
6) $-O-CH_3$,
and p is zero, 1, 2, 3 or 4
g) $R^2$ and $R^3$, $R^2$ and $R^5$ or $R^4$ and $R^5$, together with the two nitrogen atoms to which they are bonded, form
  1) a monocyclic 5-, 6- or 7-membered heterocyclic ring, where the said ring is saturated or unsaturated and mono- or polysubstituted by
    1.1 a hydrogen atom,
    1.2 a halogen atom,
    1.3 $-O-(C_1-C_5)$-alkyl,
    1.4 oxo or
    1.5

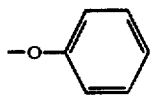

or
  2) a bicyclic 9- or 10-membered heterocyclic ring system, where this ring system is unsaturated and mono- or polysubstituted as defined in g) 1.1 to g) 1.5 or 2 carbon atoms in this ring system are replaced by nitrogen atoms, or
h) $R^1$ and $R^2$ or $R^3$ and $R^4$, together with the nitrogen atoms to which they are bonded, form a mono- or bicyclic 3- to 10-membered ring, where the ring is saturated or unsaturated and mono- or polysubstituted as defined in g) 1.1 to g) 1.5,
i) $R^1$, $R^2$, $R^3$ or $R^4$ is a mono- or bicyclic 3- to 10-membered ring, where the ring is saturated or unsaturated and mono- or polysubstituted as defined in g) 1.1 to g) 1.5, or
j) $R^2$ is

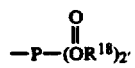

where $R^{18}$ is
a) a hydrogen atom,
b) $(C_1-C_5)$-alkyl, straight-chain or branched, or
c) phenyl,
l is an integer from 0 to 7,
m is zero, 1 or 2,
n is an integer from 0 to 7,
the sum of the numbers l, m and n is equal to 10 or less than 10,
$R^8$, $R^9$, $R^{10}$ and $R^{11}$ are identical or different and independently of one another have the meaning below
a) a hydrogen atom,
b) $(C_1-C_5)$-alkyl, straight-chain or branched, or
c) phenyl,
X is
a) a hydrogen atom,
b) hydroxyl,
c) a halogen atom, or
d) $(C_1-C_4)$-alkyl, in the case in which l, m and n are zero,
excluding the compound tetraethyl 1-((aminoiminomethyl)amino)methane-1,1-bisphosphonate.

2. A compound of the formula Ia, Ib or Ic as claimed in claim 1, or an alkali metal, ammonium or triethylammonium salt of the compound of the formula Ia, Ib or Ic, in which $R^1$, $R^2$, $R^3$, $R^4$, $R^5$, $R^6$ and $R^7$ are identical or different and independently of one another have the meaning below
a) a hydrogen atom,
b) $(C_1-C_7)$-alkyl, straight-chain or branched,
c) $(C_5-C_8)$-cycloalkyl,
d) a radical of the formula II,
  in which $R^{12}$, $R^{13}$ or $R^{14}$ are identical or different and independently of one another have the meaning below
  1) a hydrogen atom,
  2) a halogen atom,
  $(C_1-C_5)$-alkyl, straight-chain or branched,
  4) $(C_1-C_5)$-alkyl, straight-chain or branched, mono- or polysubstituted by
    4.1 a halogen atom,
  5) $-(SO_2)-CH_3$ or
  6) $-O-CH_3$,
  and p is zero, 1, 2 or 3,
e) $R^2$ and $R^3$, $R^2$ and $R^5$ or $R^4$ and $R^5$, together with the two nitrogen atoms to which they are bonded, form
  1) a monocyclic 5-, 6- or 7-membered heterocyclic ring, where said ring is saturated or unsaturated and mono- or polysubstituted by
    1.1 a hydrogen atom,
    1.2 $-O-(C_1-C_5)$-alkyl,
    1.3 oxo or
    1.4

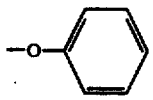

or 2) a bicyclic 9- or 10-membered heterocyclic ring system, where this ring system is unsaturated and mono- or polysubstituted as defined in e) 1.1 to e) 1.4 and/or 2 carbon atoms in this ring system are replaced by nitrogen atoms, or f) $R^1$ and $R^2$ or $R^3$ and $R^4$, together with the nitrogen atoms to which they are bonded, form a mono- or bicyclic 3- to 10-membered ring, where the ring is saturated or unsaturated and mono- or polysubstituted as defined in e) 1.1 to e) 1.4, or g) $R^2$ is

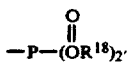

where $R^{18}$ is
a) a hydrogen atom or
b) $(C_1-C_4)$-alkyl, straight-chain or branched;
X is
a) a hydrogen atom or
b) hydroxyl;
l is an integer from 0 to 5;
m is zero or 1;
n is an integer from 0 to 5;
the sum of the numbers l, m and n is equal to 7 or less than 7;
$R^8$, $R^9$, $R^{10}$ and $R^{11}$ are identical or different and independently of one another have the following meaning
a) a hydrogen atom or
b) $(C_1-C_4)$-alkyl, straight-chain or branched.

3. A compound of the formula Ia, Ib or Ic as claimed in claim 1 or a sodium, potassium, ammonium or triethylammonium salt of the compound of the formula Ia, Ib or Ic,
in which $R^1$ is
a) a hydrogen atom or
b) $(C_1-C_3)$-alkyl,
$R^2$ is
a) a hydrogen atom,
b) $(C_1-C_3)$-alkyl,
c) $(C_5-C_8)$-cycloalkyl or
d)

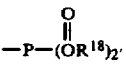

where $R^{18}$ is
1) a hydrogen atom or
2) $(C_1-C_4)$-alkyl, $R^3$, $R^4$, $R^5$ or $R^7$ are a hydrogen atom, or
$R^2$ and $R^3$, $R^2$ and $R^5$ or $R^4$ and $R^5$, together with the two nitrogen atoms to which they are bonded, form a monocyclic 5-, 6- or 7-membered ring, where the ring is saturated or unsaturated, or
$R^1$ and $R^2$ or $R^3$ and $R^4$, together with the nitrogen atom to which they are bonded, form a mono- or bicyclic 3- to 10-membered ring, where the ring is saturated or unsaturated,
$R^6$ is
a) a hydrogen atom or
b) $(C_5-C_8)$-cycloalkyl, or
$R^8$, $R^9$, $R^{10}$ or $R^{11}$ are identical or different and independently of one another have the meaning below
a) a hydrogen atom,
b) $(C_1-C_4)$-alkyl,
X is a hydrogen atom or hydroxyl,
l is an integer from 0 to 3,
m is zero or 1,
n is an integer from 0 to 3
the sum of the numbers l, m and n is equal to 5 or less than 5.

4. A compound as claimed in claim 1 selected from tetraethyl 2-((O,O-diisobutylphosphoryl)-(aminoiminomethyl)amino)ethane-1,1-bisphosphonate,
2-((aminoiminomethyl)amino) ethane-1,1-bisphosphonic acid, tetraethyl 4-((bis(1,1-dimethylethoxycarbonyl)aminoiminomethyl)amino)butane-1,1-bisphosphonate,
tetraethyl 2-((benzimidazolaminoiminomethyl)amino)ethane-1,1-bisphonate,
2-((benzimidazolaminoiminomethyl)amino)ethane-1,1-bisphonic acid and
4-((aminoiminomethyl)amino)butane-1,1-bisphosphonic acid.

5. A pharmaceutical composition containing an effective amount of at least one compound of the formula Ia, Ib or Ic as claimed in claim 1, or at least one physiologically tolerable salt of a compound of the formula Ia, Ib or Ic in addition to a physiologically acceptable auxiliary or excepient.

6. A pharmaceutical composition as claimed in claim 5 also containing another additive or another active compound.

7. A method for the prophylaxis or treatment of osteoporosis which comprises administering to a mammal in need of such treatment a pharmaceutical composition as claimed in claim 5.

8. A method for the prophylaxis or treatment of osteoporosis which comprises administering to a mammal in need of such treatment an effective amount of a compound of the formula Ia, Ib or Ic as claimed in claim 1 or a physiologically tolerable salt of the compound of the formula Ia, Ib or Ic.

9. A method for the prophylaxis or treatment of osteoporosis which comprises administering to a mammal in need of such treatment an effective amount of tetraethyl 1-((aminoiminomethyl)amino)methane-1,1-bisphosphonate or a physiologically tolerable salt thereof.

* * * * *

UNITED STATES PATENT AND TRADEMARK OFFICE
CERTIFICATE OF CORRECTION

PATENT NO. : 5,294,608

DATED : March 15, 1994

INVENTOR(S) : Hans-Jochen LANG et al.

It is certified that error appears in the above-identified patent and that said Letters Patent is hereby corrected as shown below:

Title page,
item [75] Inventors, line 5, "Anne-Marie Moura, Moura" should read --Anne-Marie Moura, Paris--.

Claim 2 at column 20, line 52, "$(C_1-C_5)$alkyl" should read --3) $(C_1-C_5)$alkyl--.

Claim 4, at column 22, line 31 "bisphonate" should read --bisphosphonate--.

Claim 4, at column 22, line 33 "bisphonic" should read --bisphosphonic--.

Signed and Sealed this

Thirteenth Day of December, 1994

*Attest:*

BRUCE LEHMAN

*Attesting Officer*     *Commissioner of Patents and Trademarks*